US011366067B2

(12) United States Patent
Hsu et al.

(10) Patent No.: US 11,366,067 B2
(45) Date of Patent: Jun. 21, 2022

(54) SYSTEM AND METHOD FOR EVALUATING FLAVOR OF FOOD BASED ON GAS

(71) Applicant: TAIWAN CARBON NANO TECHNOLOGY CORPORATION, Miaoli County (TW)

(72) Inventors: Ching-Tung Hsu, Miaoli County (TW); Chun-Wei Shih, Miaoli County (TW); Kuang-Che Lee, Miaoli County (TW); Chia-Hung Li, Miaoli County (TW); Chien-Yao Huang, Miaoli County (TW); Chun-Hsien Tsai, Miaoli County (TW); Ting-Chuan Lee, Miaoli County (TW); Chun-Jung Tsai, Miaoli County (TW)

(73) Assignee: TAIWAN CARBON NANO TECHNOLOGY CORPORATION, Zhunan Township, Miaoli County (TW)

( * ) Notice: Subject to any disclaimer, the term of this patent is extended or adjusted under 35 U.S.C. 154(b) by 314 days.

(21) Appl. No.: 16/825,329

(22) Filed: Mar. 20, 2020

(65) Prior Publication Data

US 2020/0300774 A1 Sep. 24, 2020

(30) Foreign Application Priority Data

Mar. 22, 2019 (TW) .................................. 108110105

(51) Int. Cl.
*G01N 21/78* (2006.01)
*G01N 21/25* (2006.01)
(Continued)

(52) U.S. Cl.
CPC ......... *G01N 21/783* (2013.01); *G01N 21/251* (2013.01); *G01N 33/0001* (2013.01);
(Continued)

(58) Field of Classification Search
CPC ....... G01N 2035/00752; G01N 21/251; G01N 21/783; G01N 21/8483; G01N 21/78;
(Continued)

(56) References Cited

U.S. PATENT DOCUMENTS

2017/0160005 A1* 6/2017 Park ...................... F25D 25/005

FOREIGN PATENT DOCUMENTS

CN 107358507 A 11/2017

* cited by examiner

*Primary Examiner* — Jennifer Wecker
*Assistant Examiner* — Kathryn Elizabeth Limbaugh
(74) *Attorney, Agent, or Firm* — Muncy, Geissler, Olds & Lowe, P.C.

(57) ABSTRACT

The invention provides a system for evaluating food flavors based on a gas, including a multi-gas sensing module and an odor information processing module. The sensing module includes a colorimetric gas sensing chip for reacting with odor molecules emitted by the food to be evaluated to form a coloring reaction, and the sensing module generates a color image respectively corresponding to coloring reaction according to the coloring reaction. The processing module is communicatively connected with the sensing module and includes an image acquisition unit for converting the color image into an odor information, a database unit including a plurality of identification information, and an arithmetic unit perform a calculation to form a result for evaluating the food flavors based on the plurality of identification information and the color image. The user can judge the actual condition of foods according to the result for evaluating the food flavors.

10 Claims, 4 Drawing Sheets

(51) Int. Cl.
*G01N 33/00* (2006.01)
*G01N 33/02* (2006.01)
*G01N 35/00* (2006.01)

(52) U.S. Cl.
CPC ......... *G01N 33/0036* (2013.01); *G01N 33/02* (2013.01); *G01N 35/00732* (2013.01); *G01N 2035/00752* (2013.01)

(58) Field of Classification Search
CPC ............... G01N 31/22; G01N 33/0001; G01N 33/0036; G01N 33/02; G01N 35/00732; G06Q 30/0631; G06V 20/68
USPC ............. 422/84, 85, 86, 87, 88, 89; 436/164
See application file for complete search history.

SYSTEM AND METHOD FOR EVALUATING FLAVOR OF FOOD BASED ON GAS

FIELD OF THE INVENTION

The invention relates to the field of an e-commerce service system of raw and fresh foods, in particular to a system for evaluating food flavors utilizing a colorimetric gas sensing chip to assist food flavors judgment.

BACKGROUND OF THE INVENTION

With the evolution and popularity of Internet technology, a variety of information can immediately appear at the click of a finger. In the present, the Internet is widely applied in various fields, such as e-commerce service, and the traditional market is gradually replaced since people have benefits of the convenience and the immediacy from e-commerce. Since e-commerce becomes more popular, the relevant merchants desire to find opportunities to extend their business. For example, clothing, electric appliances, articles for daily use and the like are all involved by e-commerce, so that the basic life requirements of people can be met through e-commerce.

Among the fields of life demands such as foods, clothing, living and traveling, "food" is the most closely related to people's life. However, unlike other fields, food conditions such as tastes, freshness, and maturity of foods cannot be judged only from pictures or words provided by e-commerce on a website, and it can only be judged by a real contact to food entities. Therefore, relevant merchants propose a solution, such as Chinese Patent Publication No. CN107358507A, which mentions an Internet-based food promotion and sale system, comprising a visitor login end, a server and a member login end, wherein the visitor login end comprises a member registration module, a food evaluation system, a freight payment system and a food foretaste system; the server comprises a video information storage system and a food evaluation system; the visitor login end is connected with the server by an information query module; output ends of the food evaluation system, the freight payment system and a food foretaste application system are connected with an input end of the server by a network communication module; and the member login end comprises the food evaluation system, the freight payment system, the food foretaste system and a food purchasing system. According to the invention, a user can enter a server page by the login end, quickly find related food by the information query module in the browsing process; when it is uncertain whether the food is suitable for the taste of the user or not, a foretaste product can be freely applied, with only a little freight paid, and unnecessary cost can be reduced.

According to the prior art, the uncertainty of purchasing food by the e-commerce can be reduced, but the flavor, freshness, and maturity of the raw and fresh foods cannot be ensured by the prior art since the flavor, freshness, and maturity can be influenced by factors such as preservation environment, production place and harvesting time of the raw and fresh foods, Besides, it is difficult to guarantee the goods belong to the same source and the same quality of the flavor, freshness, and maturity even if people try the foods before they purchase the raw and fresh foods. Therefore, there is still room for a great improvement in the network e-commerce service system for raw and fresh food.

SUMMARY OF THE INVENTION

The main purpose of the present invention is to solve the problem that the food flavors cannot be rapidly and objectively presented in the prior art.

To achieve the above purpose, the present invention provides a system for evaluating food flavors based on a gas, comprising a multi-gas sensing module and an odor information processing module.

The multi-gas sensing module includes at least one colorimetric gas sensing chip for reacting with at least one odor molecule emitted by the food to be evaluated.

The odor information processing module includes an image acquisition unit which acquires at least one color image from the colorimetric gas sensing chip and converts the color image into an odor information, a database unit communicatively connected with the image acquisition unit and including a plurality of identification information, and an arithmetic unit performs a calculation to form a result for evaluating the food flavors based on the plurality of identification information and the odor information.

In an embodiment, the colorimetric gas sensing chip includes a chemical reaction layer and a coloring reaction layer stacked with each other, the chemical reaction layer and a plurality of odor molecules generate a chemical reaction, and the coloring reaction layer generates a coloring reaction according to the chemical reaction to present the color image corresponding to the food to be evaluated. The chemical reaction layer includes at least one reaction zone capable of reacting with the plurality of odor molecules to generate the chemical reaction, causing one side of the chemical reaction layer opposite to the coloring reaction layer to be served as an inlet side; the coloring reaction layer includes a coloring side and a reaction side, and the reaction side contacts the reaction zone of the chemical reaction layer; and the coloring reaction layer further includes a coloring indicator to generate a plurality of coloring reaction corresponding to the chemical reactions of the reaction side.

In an embodiment, the inlet side is further provided with at least one membrane layer selected from the group consisting of a water-resistant gas permeable membrane, an adsorbent layer, a diffusion membrane with an odor molecule screening function, and a combination thereof.

In an embodiment, the multi-gas sensing module further includes a label carried on the colorimetric gas sensing chip and a bar code structure disposed on the label and corresponding to the food to be evaluated.

In an embodiment, the color image includes a plurality of colors which are distinct from each other.

In an embodiment, the invention further includes a handheld electronic device including an application unit (APP) to provide the plurality of odor information and the plurality of identification information.

In an embodiment, the database unit is further linked to a cloud data database.

In an embodiment, the calculation further includes a real-time calculation, a near real-time calculation, an off-line calculation, or a combination thereof.

The invention further provides a method for operating a system for evaluating food flavors based on a gas, which comprises the steps of:

S1: providing a multi-gas sensing module, wherein the multi-gas sensing module includes at least one colorimetric gas sensing chip, and the colorimetric gas sensing chip includes a chemical reaction layer and a coloring reaction layer stacked with each other.

S2: enabling the colorimetric gas sensing chip to react with at least one odor molecule emitted by a food to be evaluated, generating a chemical reaction between the chemical reaction layer and the plurality of odor molecules, and enabling the coloring reaction layer to generate a coloring reaction according to the chemical reaction so as to present at least one color image corresponding to the food to be evaluated.

S3: providing an odor information processing module including an image acquisition unit, a database unit including plurality of identification information, and an arithmetic unit, enabling the image acquisition unit to acquire the color image from the colorimetric gas sensing chip and converting the color image into an odor information, and causing the arithmetic unit to perform a calculation to form a result for evaluating the food flavors based on the plurality of identification information and the odor information.

According to the invention, a more objective index can be provided for a user so as to quickly know the conditions of food, such as flavors, sweetness, maturity, freshness and the like. Due to the fact that all information is data-based, the communication between users has a specific basis. According to the invention, the user does not need to identify information such as the freshness of foods only in a subjective detection mode such as visual observation, smell screening and the like in the past, so as to further reduce the food safety crisis. Moreover, the supplier can control the production and marketing conditions of the product by the invention, and even complete a market analysis of the product so as to draw up a marketing mode more conforming to the market trend and improve the gross profit rate of overall sale. Therefore, both requirements of users and suppliers are met by the invention, and a more convenient and practical system for evaluating raw and fresh foods is provided.

DETAILED DESCRIPTION OF THE PREFERRED EMBODIMENTS

With regard to the detailed description and technical aspects of the present invention is described with reference to the accompanying drawings as follows.

Figure 1:
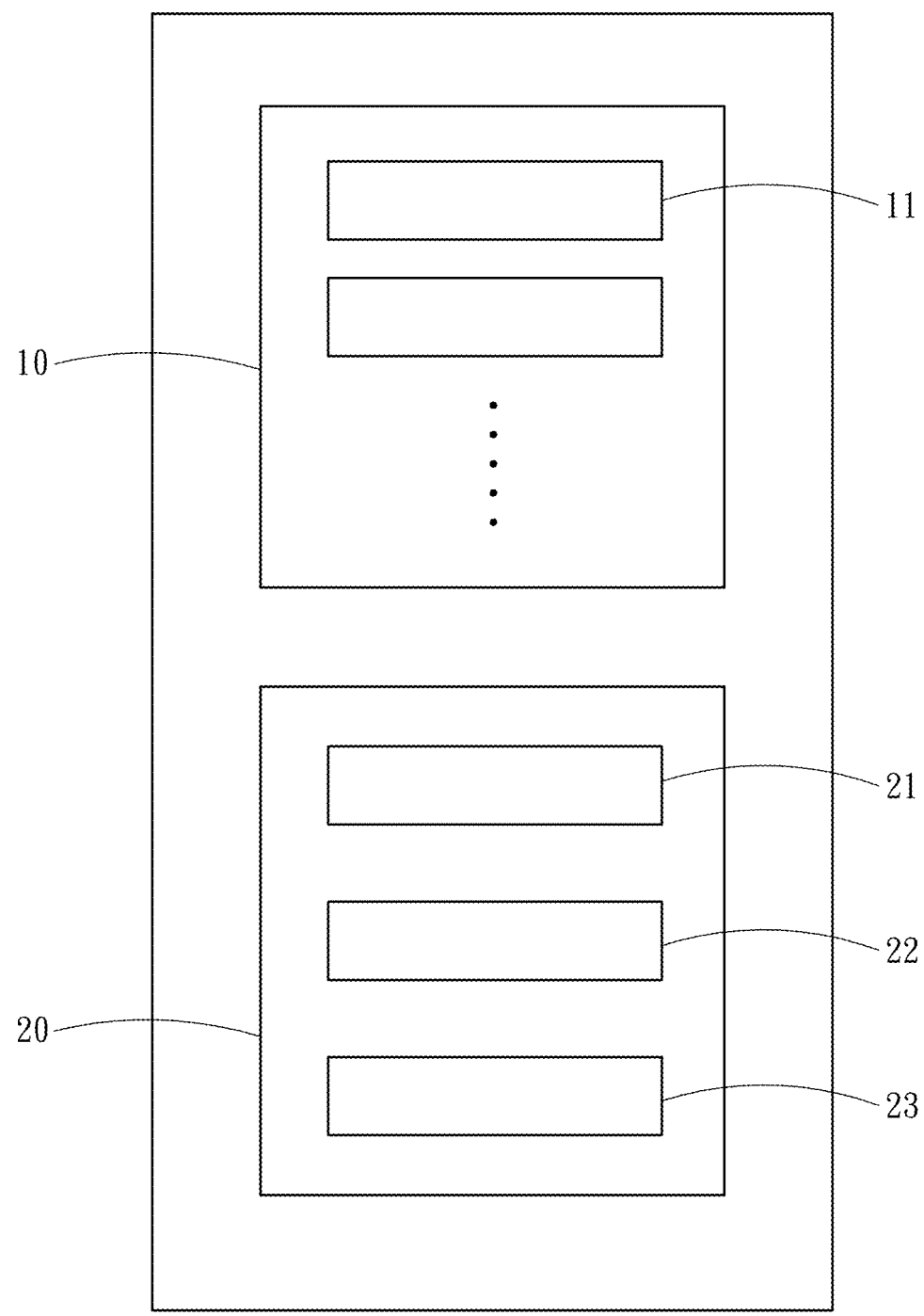
FIG. 1 is a schematic diagram showing the structure of a system according to an embodiment of the present invention.
Figure 2:
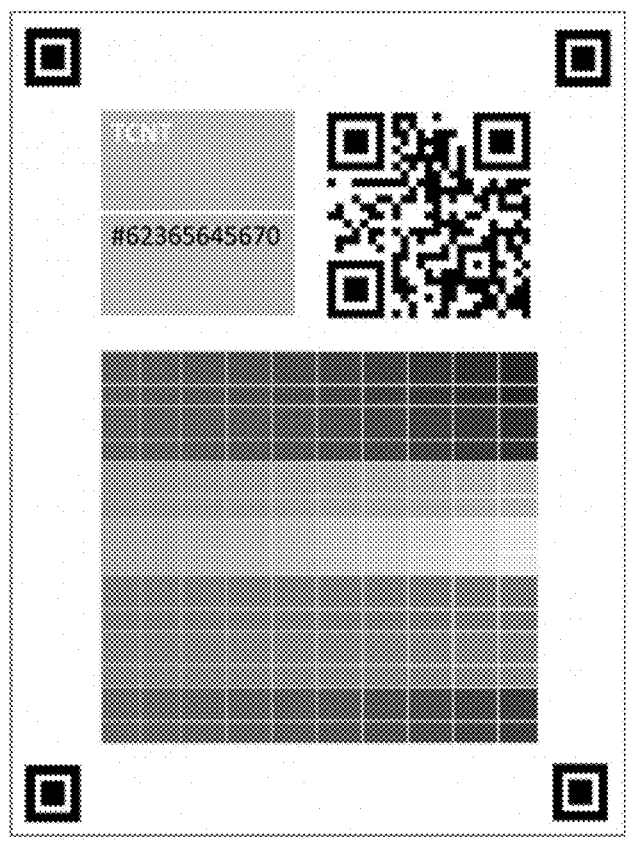
FIG. 2 is a schematic diagram showing the appearance of a colorimetric gas sensing chip according to an embodiment of the present invention.

Please refer to FIG. 1 and FIG. 2. The present invention relates to a system for evaluating flavor of food based on a gas, comprising a multi-gas sensing module 10 and an odor information processing module 20.

The multi-gas sensing module 10 includes at least one colorimetric gas sensing chip 11, and the colorimetric gas sensing chip 11 reacts with at least one odor molecule emitted by a food to be evaluated to form at least one coloring reaction. The multi-gas sensing module 10 generates at least one color image according to the coloring reaction, wherein the color image corresponds to the coloring reaction and includes a plurality of colors which are distinct from each other. In short, the multi-gas sensing module 10 forms the color images through the coloring reactions generated by the odor molecules reacting with the colorimetric gas sensing chip 11. In the present invention, the source of the food to be evaluated may be a raw and fresh food or a take-away meal. More specifically, any food capable of emitting odors such as vegetable, fruit, meat, bento, and the like can be used in the present invention, but is not limited to the foregoing mention.

Figure 3:
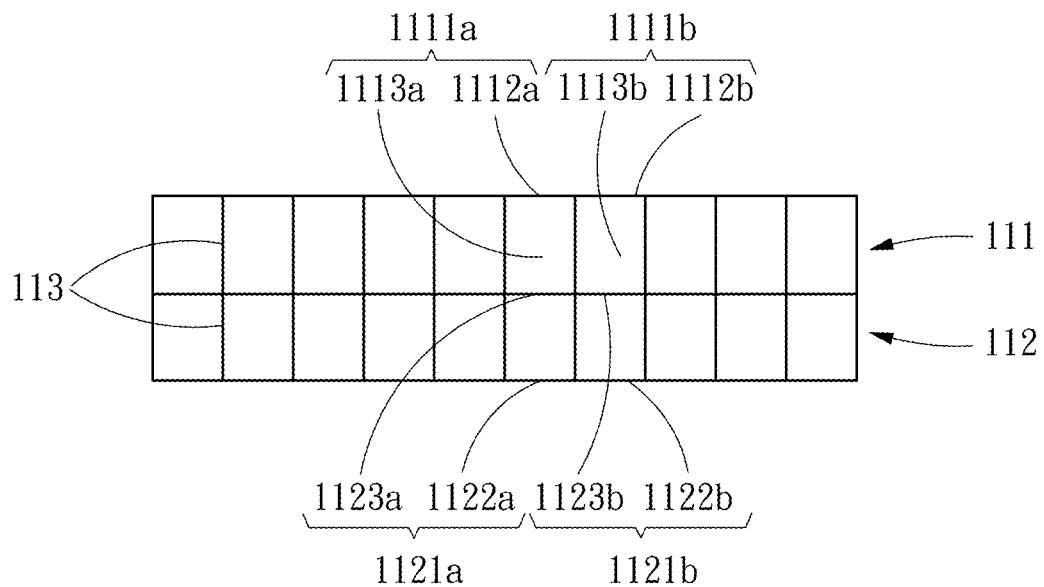
FIG. 3 is a schematic diagram showing the structure of the colorimetric gas sensing chip according to an embodiment of the present invention.
Figure 4:
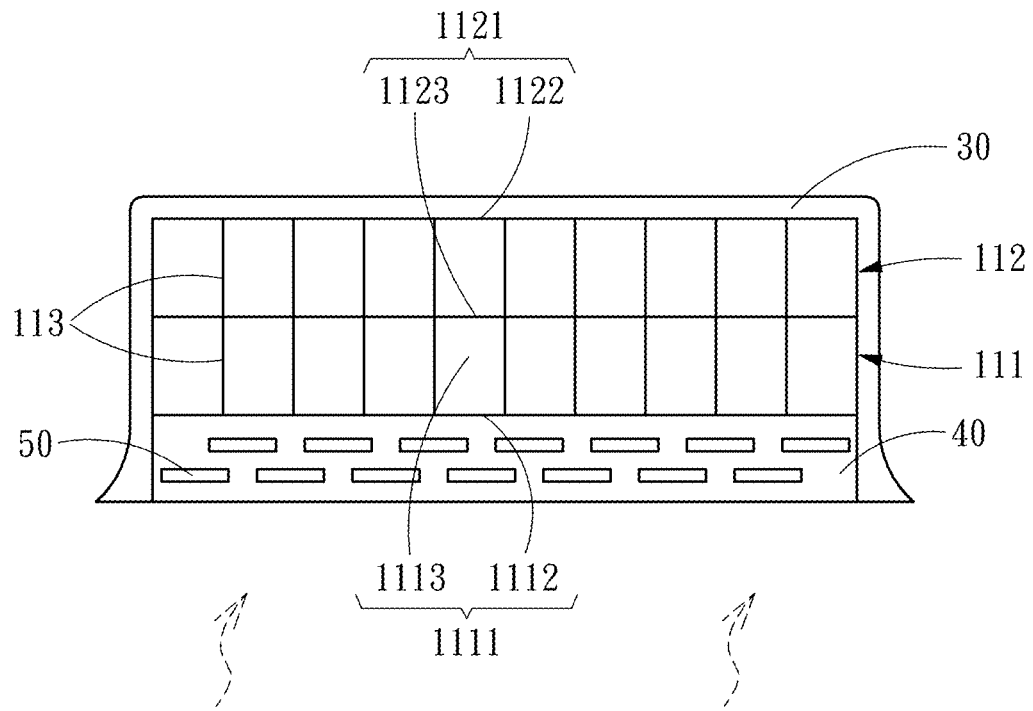
FIG. 4 is a schematic diagram showing the structure of the colorimetric gas sensing chip according to another embodiment of the present invention.

Please refer to FIG. 3 and FIG. 4. The colorimetric gas sensing chip 11 includes a chemical reaction layer 111 and a coloring reaction layer 112 stacked with each other, and the colorimetric gas sensing chip 11 further includes a partition portion 113. The colorimetric gas sensing chip 11 would be described in more detail as follows to enable those skilled in the art to more understand the present invention.

The chemical reaction layer 111 is divided into a plurality of first areas 1111 by the partition portion 113. Each of the first areas 1111 includes an inlet side 1112 opposite to one side of the coloring reaction layer 112 and a reaction zone 1113. The odor molecules enter the reaction zone 1113 from the inlet side 1112, and each of the reaction zones 1113 reacts with the odor molecules to generate a chemical reaction. Each of the reaction zones 1113 may include different types of chemicals to react with different target gases. For example, some reaction zones 1113 may react with alkanes; some reaction zones 1113 may react with alcohols; and some reaction zones 1113 may react with sulfides, etc. The partition portion 113 separates the first areas 1111 adjacent to each other so that the adjacent first areas 1111 do not affect each other. The chemical reaction may be a redox reaction, an acid-base reaction, an enzyme-catalytic reaction, a metal-catalytic reaction, a condensation reaction, a hydrolysis reaction, an addition reaction, an elimination reaction, a substitution reaction, or a combination thereof, but is not limited to foregoing mention. For example, one suitable redox reaction for the invention could be oxidizing ethanol to acetaldehyde or acetic acid, and a glucose oxidase may be used in an enzyme-catalytic reaction, and a platinum catalyst may be used in a metal-catalytic reaction. Alternatively, assuming that one of the reaction zones 1113 is coated with hydrazine ($H_2N-NH_2$), carbazic acid ($H_2NNHCOOH$) is generated when the odor molecules which include carbon dioxide react with the reaction zone 1113 coated with hydrazine, and a color is generated by using a Crystal violet used as a redox indicator. Also, in an embodiment, the colorimetric gas sensing chip 11 may further include a protective layer provided on the inlet side 1112 to prevent interference or damage caused by the gas directly entering the reaction zones 1113.

A result of the reaction is used as a history information if the reaction occurring in the reaction zones 1113 is an irreversible reaction. However, if desorption of the odor molecules occur after adsorption of the odor molecules in the reaction zones 1113, the reaction is a reversible reaction, which is used as a real-time information. Therefore, at design stage, the diffusion coefficient can be appropriately adjusted to control the adsorption and desorption speed of the odor molecules, so that the reactions in the reaction zones 1113 are reversible, and the history information and real-time information can be simultaneously recorded.

The coloring reaction layer 112 is also separated by a partition portion 113 to include a plurality of second areas 1121, the second areas 1121 and the first areas 1111 are correspondingly stacked with each other, and each of the second areas 1121 includes a coloring side 1122, and a reaction side 1123 in contact with the reaction zone 1113 of the chemical reaction layer 111. The coloring reaction layer 112 includes a coloring indicator; therefore, when the reaction zone 1113 generates the chemical reaction, the coloring reaction layer 112 in contact with the reaction zone 1113 generates a coloring reaction corresponding to the chemical reaction.

The composition of the coloring indicator is selected from the group consisting of a hydrate, a precipitate, a metal complex, and combinations thereof. Take the hydrate as an example, it can be dry cobaltous chloride which will become pink hydrate when meets water vapor; take the precipitate as an example, it can be black lead sulfide precipitate produced when lead acetate meets hydrogen sulfide; take the metal complex as an example, it can be oxygen coordinating and combining with iron ions in heme to present bright red color. The "coloring indicator" suitable for use in the present invention is not particularly limited. For example, the coloring indicator is further an acid-base indicator, a solvatochromism, or combinations thereof. For instance, the acid-base indicator may be a colorimetric reagent such as Bromohymol Blue, phenolphthalein, and the like.

In one embodiment, the first area 1111 is further divided into the first areas 1111a, 1111b, the inlet side 1112 is divided into the inlet sides 1112a, 1112b, and the reaction zone 1113 is divided into the reaction zones 1113a, 1113b. The second area 1121 is further divided into the second areas 1121a, 1121b, the coloring side 1122 is divided into the coloring sides 1122a, 1122b, and the reaction side 1123 is divided into the reaction sides 1123a, 1123b. The partition portion 113 is a partition wall separating the adjacent first areas 1111a, 1111b and the adjacent second areas 1121a, 1121b, so that the odor molecules enter the inlet side 1112a and react with the reaction zone 1113a without affecting the adjacent reaction zone 1113b, and the reaction in the reaction zone 1113a only affects the reaction side 1123a and the coloring side 1122a, without affecting the reaction side 1123b and the coloring side 1122b.

Please refer to FIG. 4. In an embodiment, an anti-reflection film 30 is further disposed at an outermost side of the colorimetric gas sensing chip 11, which helps a user to observe the color change of the coloring side 1122 through an instrument or the naked eyes from the outside without interference. At least one layer of diffusion membranes 40 including an odor molecule screening function are provided to achieve the effect of screening specific odor molecules. The diffusion membrane 40 is disposed outside the chemical reaction layer 111. In more detail, the outside the chemical reaction layer 111 is near the inlet side 1112.

In an embodiment that a plurality of diffusion membranes 40 are provided, each diffusion membrane 40 may be designed to block the different odor molecules. In addition, in an embodiment, a graphene 50 with varying sizes may be added to each diffusion membrane 40 to adjust the diffusion paths of the odor molecules in the plurality of diffusion membranes 40, and thus the diffusion speed of the molecules is changed to obtain the effect of screening macromolecules or micromolecules.

In order to more efficiently adsorb the odor molecules, the present invention may further include an adsorption molecule in the diffusion membrane 40 to achieve the above object. The adsorption molecule may be any liquid, colloids, pores, or fibrous membranes including an adsorbent function. In an embodiment, glycerol may be used as the adsorption molecule. In another embodiment, when pores are used as the adsorption molecules to screen the larger sizes of odor molecules by using the characteristics of the pores. However, it is also possible to directly dispose an adsorbent layer including the adsorption molecules between a pair of diffusion membranes 40, which can also obtain a good adsorption effect.

In addition, in the various embodiments described in the foregoing, a water-resistant gas permeable membrane may be selectively provided at an appropriate position near the inlet side 1112 of the chemical reaction layer 111, to reduce the interference of the external environment to the internal chemical reaction. In general, the membrane layer may be selected from the group consisting of the gas permeable membrane, the adsorbent layer, the diffusion membrane 40, and a combination thereof.

According to the invention, a plurality of colorimetric blocks are arranged, so that the color comparison blocks are corresponding arranged with the reaction zones 1113, and thereby the color identification is easier, and then the identification error is reduced.

In the above embodiments, the order of the chemical reaction layer 111, the coloring reaction layer 112, or other functional layers may be exchanged with one another without limitation, on the premise that the odor molecules enter the chemical reaction layer 111 and react with the reaction zones 1113.

From the above description, the colorimetric gas sensing chip 11 in the multi-gas sensing module 10 of the present invention has been described in series, and the next will describe the odor information processing module 20.

The odor information processing module 20 includes an image acquisition unit 21, a database unit 22 communicatively connected with the image acquisition unit 21 and including a plurality of identification information, and an arithmetic unit 23.

The plurality of identification information of the database unit 22 may be formed by a sensing modeling process. In the sensing modeling process, a sample is provided first, which may be a kind of food, such as, vegetables, fruits, meats and the like, also, any foods capable of emitting smell can be applied. A color image belonging to the sample is formed by using the multi-gas sensing module 10 of the invention, and then the color image is acquired by the image acquisition unit 21 and is converted into an odor information, wherein the odor information is data-based information. Finally, the odor information is subjected to cloud data processing and artificial intelligence modeling so as to establish the plurality of identification information according to the present invention. The cloud data processing and the artificial intelligence modeling should be common knowledge to those skilled in the art, and will not be described in detail. However, it will be understood by those skilled in the art that the database unit 22 may further link a cloud data database to access the identification information in real time.

In an embodiment, the invention further includes a hand-held electronic device including an application unit (APP) to provide the odor information and the plurality of identification information. That is, a user can use the hand-held electronic device on which the APP is installed to obtain information about the coloring reaction of any food, convert the information about the coloring reaction into the odor information or the identification information by the APP, and upload the odor information or the plurality of identification information to the cloud data database. The APP may have a camera function. For instance, the information about the coloring reaction may be in the form of photos.

In an embodiment, the multi-gas sensing module 10 further includes a label carried on the colorimetric gas sensing chip 11 and a bar code structure disposed on the label and corresponding to the food to be evaluated. The bar code structure on the label may be a one-dimensional bar code, a two-dimensional bar code, a pattern tag, a radio frequency identification system (RFID) electronic label, or a combination thereof, but is not limited to the foregoing mention. The user can visit a food information network via the label at any time to confirm and search the identification information about the food to be evaluated.

Specifically, in practical application of the present invention, after the multi-gas sensing module 10 acquires the color image of the food to be evaluated and the image acquisition unit 21 converts the color image into the odor information, the arithmetic unit 23 perform a calculation to form a result for evaluating the food flavors based on the plurality of identification information and the odor information, wherein the result of evaluating the food flavors can be expressed in a data-based form. The consumer can know whether the food to be evaluated is suitable for an edible range according to the result for evaluating the food flavors. For example, if the detected food is meat, the spoilage degree, the flavor or the like information of food can be immediately obtained by the invention; if the evaluated food is vegetables and fruits, it can be immediately inferred whether the maturity of the vegetables and fruits is suitable for eating by the invention.

In the present invention, the calculation further includes a real-time calculation, a near real-time calculation, an off-line calculation, or a combination thereof. The real-time calculation includes calculating a real-time comparison result, and then a user is able to easily judge whether the result for evaluating the food flavors calculated by the real-time calculation falls within an edible range through comparing the color. The near real-time calculation and the off-line calculation include a subsequent calculation, such as more accurate information of the types and concentrations of the odor molecules, even transportation and marketing information of the foods and the like. Namely, the near real-time calculation and the off-line calculation provide comprehensive information for suppliers so as to realize the actual production and marketing conditions of the foods.

Figure 5:
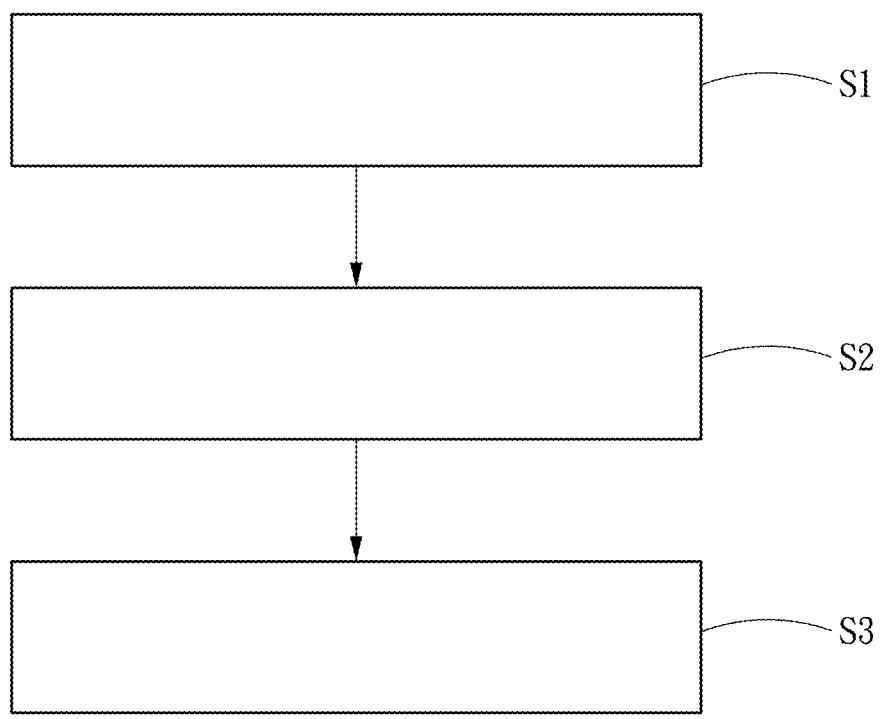
FIG. 5 is a flowchart illustrating steps of a method for operating a system according to an embodiment of the present invention.

Please refer to FIG. 5. In summary, the operation method of the present invention can be as follows:

S1: providing the multi-gas sensing module 10, wherein the multi-gas sensing module 10 includes at least one colorimetric gas sensing chip 11, and the colorimetric gas sensing chip 11 includes the chemical reaction layer 111 and the coloring reaction layer 112 stacked with each other;

S2: enabling the colorimetric gas sensing chip 11 to react with at least one odor molecule emitted by the food to be evaluated, generating the chemical reaction between the chemical reaction layer 111 and the odor molecules, and enabling the coloring reaction layer 112 to generate the coloring reaction according to the chemical reaction so as to present at least one color image corresponding to the food to be evaluated;

S3: providing the odor information processing module 20 including the image acquisition unit 21, the database unit 22 including a plurality of identification information, and the arithmetic unit 23, enabling the image acquisition unit 21 to acquire the color image from the colorimetric gas sensing chip 11 and converting the color image into the odor information, and causing the arithmetic unit 23 perform a calculation to form a result for evaluating the food flavors based on the plurality of identification information and the odor information.

According to the result for evaluating the food flavors, a user can obtain objective edible conditions that whether the food is suitable for eating; or the supplier can know the market conditions such as current production and marketing conditions so as to further conduct market evaluation.

According to the invention, a more objective index can be provided for the user, so that the user can quickly know the conditions of food, such as flavors, acidity, sweetness, maturity, freshness and the like. Due to the fact that all information is data-based, the communication between users has a specific basis. According to the invention, the user does not need to identify information such as the freshness of foods only in a subjective detection mode such as visual observation, smell screening and the like in the past, so as to further reduce the food safety crisis. Moreover, the supplier can control the production and marketing conditions of the product by the invention, and even complete a market analysis of the product to draw up a marketing project which is more conforming to the market trends and improve the gross profit rate of overall sale. Therefore, both requirements of users and suppliers are met by the invention, and a more convenient and practical system for evaluating raw and fresh foods is provided.

What is claimed is:

1. A system for evaluating food flavors based on a gas, comprising:
    a multi-gas sensing module, including at least one colorimetric gas sensing chip configured to react with at least one odor molecule emitted by a food to be evaluated; and
    an odor information processing module, including an image acquisition unit configured to acquire at least one color image from the colorimetric gas sensing chip and converts the color image into an odor information, a database unit communicatively connected with the image acquisition unit and containing a plurality of identification information, an arithmetic unit configured to perform a calculation to form a result for evaluating the food flavors based on the plurality of identification information and the odor information, and wherein the colorimetric gas sensing chip includes a chemical reaction layer and a coloring reaction layer stacked with each other, the chemical reaction layer and the odor molecules generate a chemical reaction,
    wherein the coloring reaction layer generates a coloring reaction according to the chemical reaction to present the color image corresponding to the food to be evaluated;
    wherein the chemical reaction layer includes at least one reaction zone configured to react with the odor molecules to generate the chemical reaction, wherein the chemical reaction is selected from aa redox reaction, an acid-base reaction, an enzyme-catalytic reaction, a metal-catalytic reaction, a condensation reaction, a hydrolysis reaction, an addition reaction, an elimination reaction, a substitution reaction, or a combination thereof, causing one side of the chemical reaction layer opposite to the coloring reaction layer to be served as an inlet side.

2. The system as claimed in claim 1, wherein; the coloring reaction layer includes a coloring side and a reaction side, and the reaction side contacts the reaction zone of the chemical reaction layer; and the coloring reaction layer further includes a coloring indicator to generate the coloring reaction corresponding to the chemical reaction of the reaction side.

3. The system as claimed in claim 2, wherein the inlet side is further provided with at least one membrane layer selected from the group consisting of a water-resistant gas permeable membrane, an adsorbent layer, a diffusion membrane with an odor molecule screening function, and a combination thereof.

4. The system as claimed in claim 1, wherein the multi-gas sensing module further includes a label carried on the colorimetric gas sensing chip and a bar code structure disposed on the label and corresponding to the food to be evaluated.

5. The system as claimed in claim 2, wherein the color image includes a plurality of colors which are distinct from each other.

6. The system as claimed in claim 1, wherein the system further includes a handheld electronic device including an application unit (APP) to provide the odor information and the plurality of identification information.

7. The system as claimed in claim 1, wherein the database unit is further linked to a cloud data database.

8. The system as claimed in claim 1, wherein the calculation further includes a real-time calculation, a near real-time calculation, an off-line calculation, or a combination thereof.

9. A method for evaluating food flavors based on a gas, comprising the steps of:

S1: providing a multi-gas sensing module, wherein the multi-gas sensing module includes at least one colorimetric gas sensing chip, and the colorimetric gas sensing chip includes a chemical reaction layer and a coloring reaction layer stacked with each other;

S2: enabling the colorimetric gas sensing chip to react with at least one odor molecule emitted by a food to be evaluated, generating a chemical reaction between the chemical reaction layer and the odor molecules, and enabling the coloring reaction layer to generate a coloring reaction according to the chemical reaction so as to present at least one color image corresponding to the food to be evaluated; and S3: providing an odor information processing module including an image acquisition unit, a database unit including a plurality of identification information, and an arithmetic unit, enabling the image acquisition unit to acquire the color image from the colorimetric gas sensing chip and converting the color image into an odor information, and causing the arithmetic unit to perform a calculation to form a result for evaluating the food flavors based on the plurality of identification information and the odor information.

10. The method of claim 9, wherein the calculation further includes a real-time calculation, a near real-time calculation, an off-line calculation, or a combination thereof.

\* \* \* \* \*